United States Patent [19]

Bardasz

[11] 4,169,768
[45] Oct. 2, 1979

[54] POLARIZATION EVALUATION OF METAL DEGRADATION PROCESSES

[75] Inventor: Ewa A. Bardasz, Cranford, N.J.

[73] Assignee: Exxon Research & Engineering Co., Florham Park, N.J.

[21] Appl. No.: 881,647

[22] Filed: Feb. 27, 1978

[51] Int. Cl.² .............................................. G01N 27/46
[52] U.S. Cl. .................................. 204/1 T; 204/195 C
[58] Field of Search ............. 204/1 C, 195 C; 324/29, 324/71 R

[56] References Cited

U.S. PATENT DOCUMENTS 3,337,440  8/1967  Nestor ............................. 204/195 C Primary Examiner—Aaron Weisstuch
Attorney, Agent, or Firm—F. Donald Paris

[57] ABSTRACT

An electrochemical technique and device for estimating absolute rates of metal degradation through evaluation of the stability of petroleum film at an interface such as a metal/petroleum phase/aqueous phase. Basically, there is provided a polarization cell comprising separate compartments for containing immiscible liquids. The liquids have different densities and in a typical test the first compartment contains a first phase of lighter density, such as petroleum, and the second, smaller compartment contains a second phase of relatively greater density, such as water. Electrodes are provided such that a metal rod (which is of the same metal as the component for which metal degradation information is desired) typically referred to as the "working" electrode is positioned relative to an "auxiliary" electrode and placed in contact sequentially with the petroleum phase and with the aqueous phase in order to simulate conditions occurring in field operations. By applying an external potential to the "working" electrode, the metal can be polarized both cathodically and anodically, and the degradation characteristics of the metal can be tested and evaluated.

9 Claims, 2 Drawing Figures

POLARIZATION EVALUATION OF METAL DEGRADATION PROCESSES

BACKGROUND OF THE INVENTION

It is important for persons who formulate products to be able to predict rust and/or corrosion tendencies of hardware components in a particular media containing the product. This is best accomplished by providing those individuals with a fairly accurate assessment of corrosion rates and information pertaining to the behavior of components when contacted by a particular product. Essentially, any corrosion which occurs includes two types of reactions—electrochemical and chemical, i.e. oxidation. Typically, when this procedure is followed, it involves selecting a particular product and examining its anticorrosion performance in some appropriate machine or equipment and then putting it into actual use. However, if details of the interaction processes of the various products with metal surfaces with which they would normally come into contact during actual use were known, this would lessen the need to have any extensive and expensive experimental testing.

Corrosion essentially is a deterioration process which occurs when a metal reacts with the environment. A common place where corrosive degradation occurs in a petroleum system is a metal-oil-water interface. The electrochemical mechanism of the corrosion process occurs when a pure metal comes into contact with an aqueous corrosion media. The chemical or oxidation mechanism of the corrosion process occurs either at a pure metal-vapor interface or as a follow-up to an initial electrochemical mechanism of corrosion. Both mechanisms are generally well known in the art and are discussed in detail in several texts and publications. For example, reference is made to The Corrosion Handbook, by H. H. Uhlig, John Wiley & Sons, New York, (1963).

Normal corrosion tests performed in a laboratory involve several categories depending upon the end result of the studies desired. These include studying the corrosion mechanism; selecting the most suitable system for withstanding a particular environment; determining the environment in which a particular material or system can be satisfactorily employed; or providing controls for obtaining product uniformity. The present invention is directed towards providing a product formulator with information on the mechanism of the corrosion inhibition processes. The literature has frequently recommended using what is generally referred to as a polarization method of testing to examine the anodic and cathodic behavior of corroding metals in aqueous environments.

When iron corrodes in an aqueous solution, the occurrence of the electrochemical mechanism is most prevalent at the sites where anodic and cathodic reactions take place. The metal surface can be considered as a plurality of closely spaced anode and cathode cell sections with very minimal current passing between the cells, which imposes great difficulty in making direct measurements of the polarization to obtain the necessary data. These measurements are best accomplished by forcing the metal specimen either to be positively or negatively charged in comparison to the open circuit potential, i.e. the potential characterizing the behavior of metal in the actual in-use environment. This way the entire metal specimen is either made the anode or the cathode of the cell and the current flow between working electrode and auxiliary electrode can be examined. The results then are plotted graphically as a dependence between imposed potential and observed current. The experimental value of corrosion current is established from the graph in order to evaluate the corrosion rate.

SUMMARY OF THE INVENTION

Application of the standard polarization technique to petroleum systems which are nonconductive will not work because high electricaly resistance (low conductivity) of petroleum media will hinder accurate measurement of electrical parameters. The present invention provides a laboratory technique and device for use in petroleum systems which employ petroleum fuels, petroleum lubricants and synthetic lubricants, to reveal the various degrees of antirust protection provided by these various fuels, to determine the character of rust corrosion processes occurring in petroleum lubricant blends, and to evaluate antirust protection provided by other products.

A polarization cell according to this invention comprises a main body having a first compartment for containing an oil phase and a second, smaller compartment into which is introduced an aqueous phase in the vicinity of a metal specimen, all of which closely represents a practical state of conditions occurring in field operations, particularly when the water droplets dispersed in the oil phase adsorb onto the metal specimen surface and initiate corrosion. In the upper part of the cell, the metal specimen or working electrode is positioned such that it directly faces an auxiliary electrode. Initially, the specimen is exposed for a predetermined period of time to the oil phase. Next, the corrosive medium previously introduced into the aqueous phase compartment so that it forms a miniscus, is placed into relative contact with the surface of the metal specimen which was previously contacted by the petroleum phase. At this moment the electrochemical process which takes place at the metal/petroleum phase/aqueous media interface can be studied by imposing particular potentials on the specimen working electrode, and monitoring the leakage current initiating polarization of uncoated or insufficiently coated parts of the metal specimen. Leakage current is known to be an excellent measure of uniformity and stability of inhibiting films which may be applied for preventing corrosion processes from occurring.

Use of the cell according to the invention essentially relies upon a difference in densities between the two liquids introduced into the container. The first or upper phase must be lighter (i.e., of less density) than the second or lower phase so that the liquids remain in their relative positions during evaluation and the second phase also must be a conductive liquid. Also the liquids must be incapable of mixing or attaining homogeneity, i.e. immiscible, in order that the desired interface be present. In addition to the exposure of the specimen to an oil phase and thereafter to an aqueous phase as discussed above, the invention can be used to evaluate metal degradation characteristics of metal involved in prolonged or continuous (over extended periods of time) exposure of the metal to a water phase, sequential exposure to a water phase, or the effectiveness of a water soluble inhibitor disposed in the water phase to prevent or minimize corrosion and the like. In the case of prolonged exposure, the invention can be used to evaluate specific static situations where a coated metal is exposed to water over prolonged period(s) of time.

DESCRIPTION OF THE PREFERRED EMBODIMENT

Figure 1:
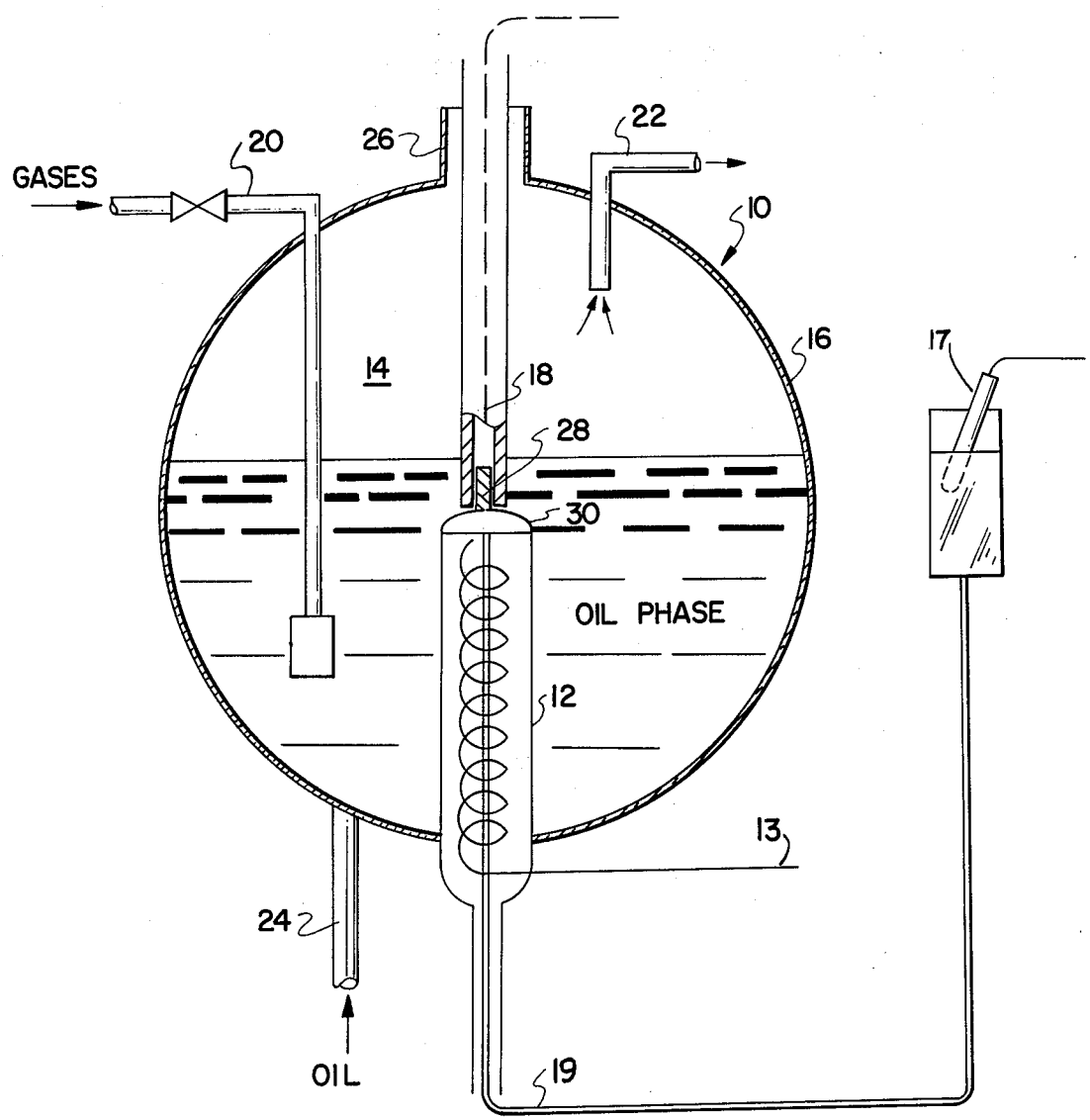
FIG. 1 illustrates schematically a typical cell for use in conducting polarization studies according to the present invention.

Referring to FIG. 1 which illustrates the experimental cell for use in conducting polarization studies to determine corrosion rates and characteristics, there is shown only for purposes of illustration a cell 10 comprising two separate compartments 12 and 14. As shown, the main body of the cell comprises a glass vessel 16 which can be a spherical, rectangular or any other wuitable shape. The inner volume thereof is separated into the two compartments, one of which comprises the small centrally located compartment 12 situated in a lower part of the vessel and having the shape of an open-ended tube. The second compartment 14 is larger and includes the remaining volume of the vessel and essentially forms the reservoir for the oil phase. The smaller compartment is connected to a supply means for receiving the aqueous phase. Also provided are three electrodes, 13 and 17 being stationary and 18 being movable. The auxiliary electrode 13 (typically made of platinum) and the Luggin-Haber connection 19 for reference electrode 17 are concentrically mounted within the aqueous phase compartment 12. The compartments are connected to supplementary inlet and outlet arrangements which forbid dispersion of gaseous phase throughout the system. The valved inlet line 20 can feed gaseous media such as oxygen, nitrogen or some corrosive gases, i.e. hydrogen sulfide into the main compartment 14 if it is desired for experimental studies and an outlet 22 exhausts any gaseous phases used preventing the system from becoming over-pressurized. The petroleum or oil phase is fed into the vessel by means of the inlet conduit 24. At the upper portion of the vessel 16 is a centrally located relatively wide opening 26 which allows introduction of the mounted working electrode 18, 28 to be described in greater detail hereinafter.

As previously described the auxiliary and reference electrodes, 13, 17, respectively, are stationary and the working electrode 18, 28 comprises a metal test specimen 28 corresponding to the material which would be in actual field use and which can be moved up and down vertically. Thus, the specimen 28 can be precisely located relative to the auxiliary electrode 13 and also relative to any petroleum-aqueous phase interface levels within the cell. To perform the experiment on the specimen, the working electrode is sequentially immersed first in the petroleum phase and then in the aqueous phase. This affords an opportunity to study interfacial processes which occur at a metal-petroleum-aqueous phase interface. Distance between the working electrode and the auxiliary electrode is accurately controlled by means of a micrometer. As shown, the cell contains the oil phase and the aqueous phase with the working electrode in contact with the meniscus 30 formed at the top of the aqueous phase compartment. The meniscus serves the purpose of providing a spacing for separating the electrodes.

The procedure for operating the cell according to the present invention essentially involves preparing the metal specimen, the metal inhibition period and then corrosion inhibition testing. First, the metal specimen which has been ground and cleaned is placed in an appropriate holder into the polarization cell. The entire cell can be mounted in a thermostat box which permits carrying out experiments at elevated temperatures and evaluating the thermodynamics of the processes observed. Next, the inlets are connected with the necessary oil and aqueous fluid reservoirs. The distance between the auxiliary electrode and the working electrode then is measured and the capillary 19 is filled with an electrolyte solution to comprise the reference electrode. Thereafter, the aqueous phase is introduced from the reservoir into the compartment 12 such that the level forms the meniscus 30 with completely covers the auxiliary electrode 13. The petroleum phase then is introduced into the larger compartment 14 of the cell with a fluid level maintained approximately one-half inch higher than the meniscus level of aqueous phase formed above the auxiliary electrode. The electrodes of the auxiliary and working electrodes then are connected to a suitable power supply from a potentiostat (e.g. Princeton Applied Research (PAR), Model 173). The reference electrode then is positioned and connected to the potentiostat. The working electrode 18 is lowered to the point of immersion in the petroleum phase for a predetermined period of time. This is referred to as the metal inhibition step or period. Time can range from 5–15 minutes or longer depending on the type of system tested. After the inhibition period is over, the working electrode is lowered to a preassigned distance from auxiliary electrode 19, and immersed into the meniscus 30 formed by the aqueous phase. An external potential is imposed on the working electrode by means of the potentiostat, biasing the electrode negatively, and the cathodic current between the working electrode and auxiliary electrode 13 is observed by means of an ammeter and the cathodic current between the electrodes also is automatically recorded on a suitable recording instrument. A voltage applied to specimen 28 then can be changed stepwise using the variable voltage controls on the potentiostat, manually or automatically.

The next step includes gathering anodic polarization data. After the working electrode, i.e. the iron specimen 28, has again been exposed for a period of time to the oil phase it is lowered further such that it is immersed into the aqueous phase to contact the meniscus surface in order to form a three-phase interface. Again the relative position of the working electrode to the auxiliary electrode is adjusted by means of a micrometer. At this point, the electrochemical process which occurs at the iron petroleum phase conductive media interface can be studied and leakage current can be studied by imposing specific anodic potentials on the working electrode. The anodic current is then measured and recorded on an appropriate recorder similar to that used for the cathodic current measurement. Thereafter, the anodic voltage applied to the working electrode is varied stepwise in accordance with a suitable method, manually or automatically.

Figure 2:
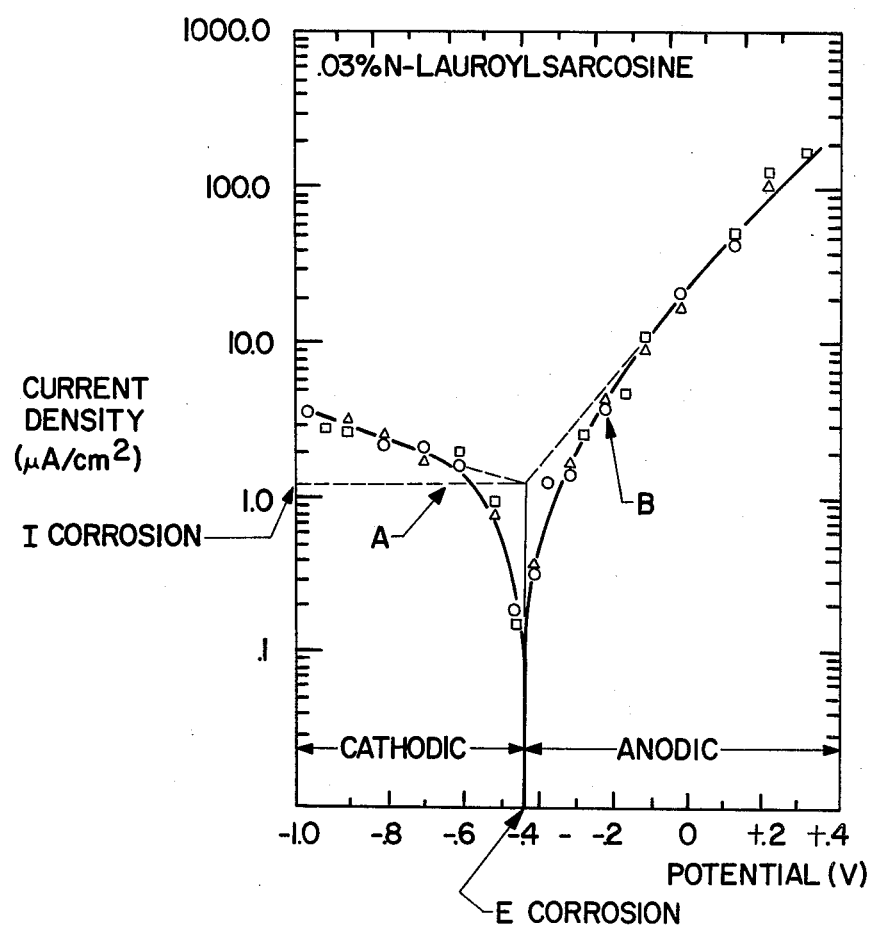
FIG. 2 is a polarization diagram for a typical evaluation showing the relation between potential imposed onto a working electrode vs. polarization current.

The final step is plotting the current versus potential data on semilogarithmic paper, and evaluating corrosion rates utilizing conventional extrapolation techniques. A typical data plot is shown in FIG. 2. This shows a polarization diagram obtained for a solution of N-Lauroyl Sarcosine in Solvent 150 N exposed to distilled water environment. The measured polarization current density is plotted against the potential imposed onto the working electrode. The two branches (A and B) represent two experimental cases, i.e., A is obtained when the working electrode acts as a cathode and B is obtained when the working electrode acts as an anode.

In order to evaluate the corrosion rates the linear portions of the graph must be extrapolated to the open circuit corrosion potential (E corrosion) which is characteristic for each system tested in order to obtain the absolute value of corrosion current (I corrosion). The data of FIG. 2 was compiled for 0.03% wt. solution of N-Lauroyl Sarcosine (as antirust inhibitor) in solvent 150 neutral. The results shown represent three independent runs.

This data is obtained by varying the voltage applied to the working electrode, reading the measured current and then calculating the current density dividing the measured current by the cross-sectional area of the working electrode (and then plotting that determined value against the voltage applied. The diagram then will show the rate of corrosion which can be expected from the metal during in-field use having the same characteristics used during the evaluation.

What is claimed is:

1. A polarization cell for use in estimating rates of metal degradation of a metal test specimen which occurs at metal/liquid interfaces, comprising: a first compartment which contains a first liquid phase at a first level; a second compartment disposed at least in part within said first liquid phase and which contains a second, conductive liquid phase at a second level and is immiscible and of greater density relative to said first phase, said first level being above said second level; a first electrode being disposed within said second liquid phase in said second compartment; and a second electrode comprising said metal test specimen being disposed within said first liquid phase at a predetermined distance spaced from said first electrode and also in contact with said second phase and capable of accepting an imposed potential, said test specimen having a surface in contact with said second phase which is smaller in size than the corresponding dimension of said second compartment, so that said test specimen electrode is capable of insertion into said second compartment, whereby said cell simulates conditions which occur in field operations involving metal corresponding to said metal test specimen.

2. The polarization cell of claim 1 including a reference electrode disposed in said second compartment proximate said first electrode for obtaining accurate measurements from said cell.

3. The polarization cell of claim 1 wherein said first phase comprises a petroleum medium and said second phase comprises a conductive aqueous medium.

4. The polarization cell of claim 3 wherein said aqueous medium has a meniscus formed at the top of said second compartment and said second electrode is coated with said first phase and in contact with said meniscus.

5. The polarization cell of claim 1 wherein said second electrode is vertically movable for placement at a desired distance relative to said first electrode.

6. A method for evaluating metal degradation comprising the steps of: placing a metal specimen comprising a first electrode into a cell comprising a first compartment containing a first nonconductive liquid phase and immersing said first electrode into said first liquid phase for a predetermined period of time sufficient to form a film on at least a surface thereof with said first phase; providing a second compartment in said cell containing a second, conductive liquid phase in contact with said first liquid phase; said surface being smaller in size than the corresponding dimension of said second compartment; immersing said surface with said film in said second, conductive liquid phase at a desired distance spaced from a second electrode; applying an external potential between said first and second electrodes; and monitoring the current flow between said first and second electrodes.

7. The method of claim 6 including exposing said surface with said film to said second, conductive liquid for a predetermined period.

8. The method of claim 6 including repetitively exposing said surface with said film to said second, conductive liquid phase.

9. The method of claim 6 including introducing a gaseous phase into said first liquid phase.

* * * * *